(12) United States Patent
Bachus et al.

(10) Patent No.: US 8,246,693 B2
(45) Date of Patent: Aug. 21, 2012

(54) RELEASIBLE ATTACHMENT SYSTEM FOR A PROSTHETIC LIMB

(75) Inventors: Kent N. Bachus, Salt Lake City, UT (US); Jeremy D. Borchert, Holladay, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 983 days.

(21) Appl. No.: 11/995,875

(22) PCT Filed: Jul. 12, 2006

(86) PCT No.: PCT/US2006/026837
§ 371 (c)(1),
(2), (4) Date: Jul. 23, 2008

(87) PCT Pub. No.: WO2007/018904
PCT Pub. Date: Feb. 15, 2007

(65) Prior Publication Data
US 2008/0288087 A1    Nov. 20, 2008

Related U.S. Application Data

(60) Provisional application No. 60/701,189, filed on Jul. 20, 2005, provisional application No. 60/767,440, filed on Mar. 28, 2006.

(51) Int. Cl.
*A61F 2/60* (2006.01)
(52) U.S. Cl. ............................................ 623/32; 623/35
(58) Field of Classification Search ..................... 623/27, 623/33, 35, 44, 32
See application file for complete search history.

(56) References Cited

U.S. PATENT DOCUMENTS

| 3,987,498 A | 10/1976 | Mason |
| 6,106,559 A | 8/2000 | Meyer |
| 6,797,008 B1 | 9/2004 | Arbogast |
| 2002/0103544 A1 | 8/2002 | McDowell |
| 2008/0058957 A1 * | 3/2008 | Newcombe et al. ............ 623/32 |

FOREIGN PATENT DOCUMENTS

EP    1309297    8/2001
(Continued)

OTHER PUBLICATIONS

International Search Report and Written Opinion of the International Searching Authority, International Patent Application No. PCT/US2011/023008, mailed May 17, 2011.

(Continued)

*Primary Examiner* — Bruce E Snow
(74) *Attorney, Agent, or Firm* — Michael Best & Friedrich LLP

(57) ABSTRACT

A releasable attachment system is provided for use with a bone anchored post and related external prosthesis such as a prosthetic limb or the like, wherein the attachment system includes a safety release mechanism designed to release or break away when encountering an excess mechanical load. The bone anchored mounting post is implanted for direct affixation to patient bone, and carries or is connected to a fixator structure protruding through soft skin tissue and the like at the end or stump of an amputated limb for mechanical connection to the external prosthesis. The safety release mechanism accommodates substantially normal patient movement throughout a corresponding range of substantially normal mechanical loads, but releases in the presence of an excess load to prevent undesirable fracture failures.

23 Claims, 14 Drawing Sheets

FOREIGN PATENT DOCUMENTS

| | | |
|---|---|---|
| EP | 1309297 B1 | 8/2001 |
| GB | 2 411 841 | 9/2005 |
| WO | 0213733 | 2/2002 |
| WO | 0213733 A2 | 2/2002 |
| WO | 2005087145 | 9/2005 |
| WO | 2005087145 A1 | 9/2005 |
| WO | 2007/018904 | 2/2007 |

OTHER PUBLICATIONS

European Patent Office Extended Search Report, European Patent Application No. 06786856.2, dated May 14, 2009.

European Patent Office Communication and Replacement Supplementary European Search Report, European Patent Application No. 06786856.2, dated Jun. 24, 2009.

European Patent Office Examination Report, European Patent Application No. 06786856.2, dated Aug. 17, 2010.

International Search Report, International Patent Application No. PCT/US06/26837, dated Jan. 18, 2007.

International Preliminary Report on Patentability, International Patent Application No. PCT/US06/26837, dated Jan. 22, 2008.

Extended European Search Report for EP application No. 11178628.1 dated Nov. 3, 2011.

* cited by examiner

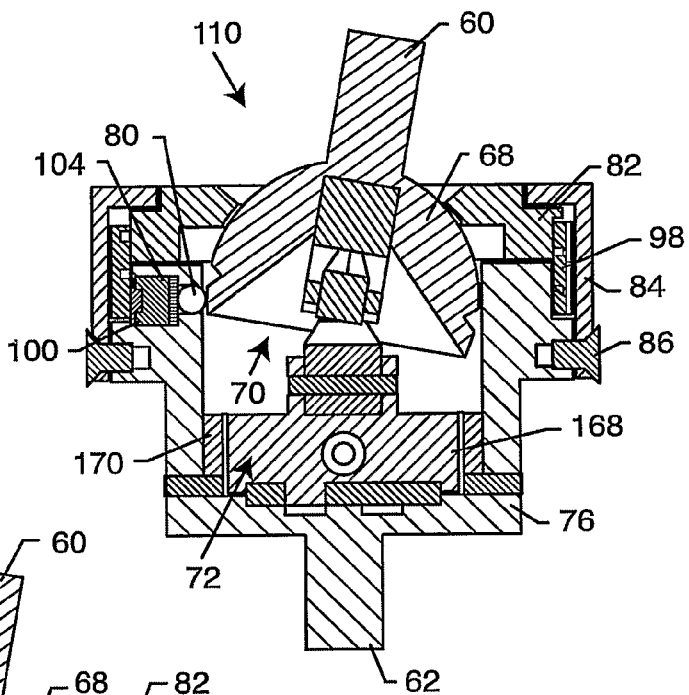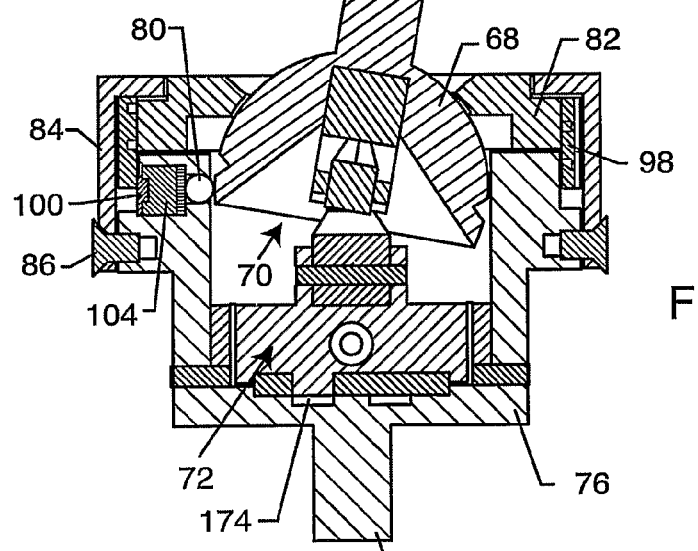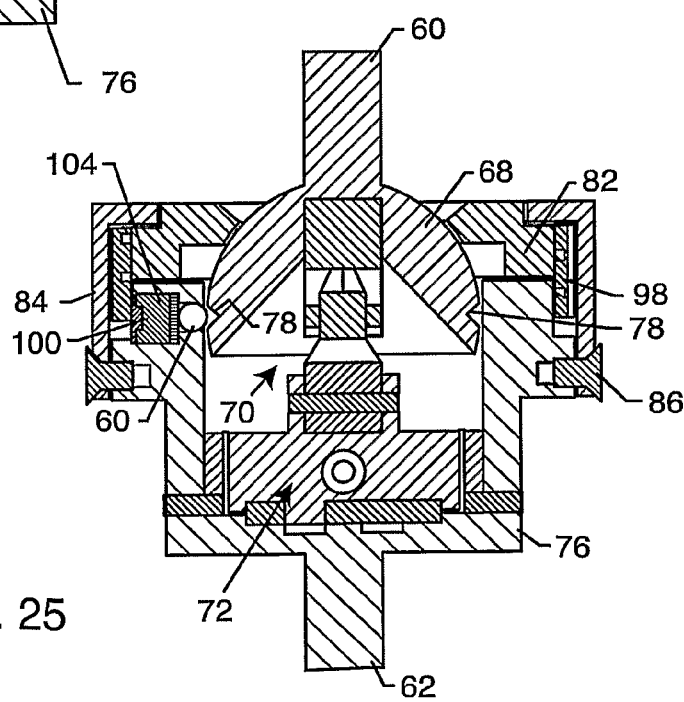

RELEASABLE ATTACHMENT SYSTEM FOR A PROSTHETIC LIMB

BACKGROUND OF THE INVENTION

This invention relates generally to improvements in external or exoskeletal prosthetic devices and systems of the type utilizing an implanted, bone anchored mounting post having or carrying an externally protruding or externally exposed fixator structure for removable attachment to a prosthesis such as a prosthetic limb or the like. More particularly, this invention relates to an improved attachment system for coupling the external fixator structure to the prosthesis, wherein the attachment system includes a safety release mechanism adapted to release in response to an excess mechanical load applied to the prosthesis.

Socket type prosthetic limbs such as prosthetic arm and leg structures for use by amputees are generally well known in the art, wherein a prosthesis is constructed with an open-ended and typically padded socket structure for receiving and supporting the post-surgical stump of an amputated limb. By way of example, a socket type prosthetic leg includes such open-ended socket structure at an upper end thereof for receiving and supporting the post-surgical upper leg of a transfemoral amputee. Various straps and/or other fasteners are provided for securing the prosthetic leg to the amputated limb to accommodate walking mobility at least on a limited basis. Such prosthetic limbs can be an important factor in both physical and mental rehabilitation of an amputee.

However, socket type prosthetic limbs are associated with a number of recognized limitations and disadvantages. In particular, the socket style prosthesis inherently couples mechanical loads associated with normal ambulatory activity through a soft tissue interface defined by the soft tissue covering the end or stump of the amputated limb, but wherein this soft tissue interface is structurally unsuited for this purpose. While many different arrangements and configurations for the requisite straps and other fasteners have been proposed for improved transmission and distribution of these mechanical loads to bone structures to achieve an improved secure and stable prosthesis attachment, to correspondingly accommodate a more natural ambulatory movement, such arrangements have achieved only limited success. In addition, compressive loading of the soft stump tissue interface often results in blisters, sores, chafing and other undesirable skin irritation problems which have been addressed primarily by adding soft padding material within the socket structure. But such soft padding material undesirably increases the extent of the soft or non-rigid interface between the amputated limb and prosthesis, all in a manner that is incompatible with an optimally secure and stable prosthesis connection. As a result, particularly in the case of a prosthetic leg, traditional socket style connection structures and methods have generally failed to accommodate a normal walking motion.

In recent years, improved external or exoskeletal prosthetic devices have been proposed, wherein the external prosthesis is structurally linked by means of a bone anchored mounting system directly to patient bone. In such devices, a rigid mounting post is surgically implanted and attached securely to patient bone as by means of osseointegration or the like. This implanted bone anchored mounting post extends from the bone attachment site and includes or is attached to a fixator pin or post structure that protrudes through the overlying soft stump tissue at the end of the amputated limb. Thus, one end of the fixator structure is externally exposed for secure and direct mechanical attachment to a prosthetic limb or the like by means of a rigid linkage.

In such bone anchored mounting systems, mechanical loads on the prosthetic limb during ambulation are thus transmitted by the rigid linkage and through the external fixator structure and implanted mounting post directly to patient bone. As a result, conventional and undesirable mechanical loading of the soft tissue interface is avoided, and substantially improved and/or substantially normal patient movements are accommodated. In addition, the requirement for compressive loading of the soft tissue at the end of the amputated limb is significantly reduced, to correspondingly reduce incidence of blisters and other associated skin irritation problems. Moreover, by mechanically linking and supporting the prosthesis directly from patient bone, amputees have reported a significant increase in perception of the prosthesis as an actual and natural body part—a highly desirable factor referred to as "osseoperception".

Although use of a bone anchored mounting system offers potentially dramatic improvements in secure and stable prosthetic limb attachment, and corresponding improvements in amputee lifestyle, major complications can arise when the prosthetic structure encounters a mechanical load that exceeds normal design parameters. More particularly, in the event of a tensile, bending, or torsion load exceeding structural design limitations, fracture-failure can occur. Breakage of prosthesis structures such as the implanted bone anchored mounting post often requires repair by surgery. Breakage of the patient bone at or near the interface with the implanted mounting post also requires surgical repair, and reseating or replacement of the implanted mounting post may not be possible. Both of these failure modes represent traumatic and highly undesirable complications.

There exists, therefore, a significant need for further improvements in and to external or exoskeletal prosthetic devices of the type utilizing a bone anchored mounting post, wherein an improved attachment system couples the prosthetic device to an externally protruding fixator structure in a manner accommodating substantially normal patient movement and a corresponding range of normal mechanical loads, but wherein the improved attachment system includes a safety release mechanism adapted to release in response to an excess mechanical load thereby preventing undesirable fracture failures. The present invention fulfills these needs and provides further related advantages.

SUMMARY OF THE INVENTION

In accordance with the invention, an improved releasable attachment system is provided for use in combination with a bone anchored post and related external prosthesis such as a prosthetic limb or the like adapted for connection thereto. The bone anchored mounting post comprises an implant component adapted for secure and stable affixation to patient bone. This bone anchored mounting post carries or is connected to a fixator structure such as an elongated pin which protrudes through soft skin tissue and the like covering the end or stump of an amputated limb, and is adapted for secure and stable attachment to the external or exoskeletal prosthesis. The improved attachment system incorporates a safety release mechanism designed to accommodate substantially normal patient movement and a corresponding range of substantially normal mechanical loads. However, in the event of an excess mechanical load applied to the prosthetic structures and/or to the implant interface of the mounting post with patient bone, the safety release mechanism is designed to release or break away thereby preventing undesirable fracture failure modes. The safety release mechanism is designed for response to excessive bending, tensile, and/or torsion loads.

In a preferred form, the releasable attachment system is interposed between the prosthesis and the fixator structure, and is adapted for mechanical connection with a radially enlarged mounting flange on the fixator structure. The safety release mechanism includes an upper socket member lined by a plurality of spring-loaded jaw elements for releasable clamp-on, substantially snap-fit engagement with the fixator structure mounting flange. The socket member is coupled by a resilient tension band to a lower release clutch including a plurality of downwardly presented, radially open detent seats having a sawtooth geometry or the like for respectively receiving a plurality of radially projecting detent pins. The tension band normally draws and retains the detent pins securely within the detent seats.

Upon encountering a bending force exceeding a predetermined limit, the tension band accommodates relative movement between the upper socket member and the lower release clutch, while the spring-loaded jaw elements accommodate relative movement between the socket member and the fixator structure mounting flange. When the bending force exceeds a predetermined limit, the jaw elements will accommodate separation of the socket member from the fixator structure. Similarly, upon encountering a tensile force load exceeding a predetermined limit, the tensile band will elongate and/or the spring-loaded jaw elements will displace to accommodate similar relative motions between components of the attachment system. Upon encountering a torsion force load exceeding a predetermined limit, the tensile band will elongate sufficiently to accommodate relative rotational displacement between the detent pins and the detent seats.

In an alternative preferred form of the invention, the attachment system or unit comprises a bending force clutch for adjustably responding to a bending force overload condition, and a torsion force clutch for adjustably responding to a torsion force overload condition. The bending force clutch comprises a relatively large ball-shaped member having a peripheral groove for normally seated reception of an array of spring-loaded clutch balls. This ball member is coupled by means of a universal joint linkage with the torsion force clutch comprising a torque cartridge including spring-loaded detent balls carried within a generally cup-shaped unit housing. The ball member and the unit housing are adapted for connection between the bone anchored fixator structure and the prosthesis. The ball member is designed for angular movement relative to the housing in response to a bending force overload condition, whereas the torque cartridge is designed for rotational movement relative to the housing in response to a torsion force overload condition.

Other features and advantages of the present invention will become apparent from the following more detailed description, taken in connection with the accompanying drawing which illustrate, by way of example, the principals of the present invention.

BRIEF DESCRIPTION OF THE DRAWINGS

The accompanying drawings illustrate the invention. In such drawings:

FIG. 23 is an enlarged anterior-posterior sectional view similar to FIG. 22, but showing a ball member displaced to a released position in response to a force overload condition;

FIG. 24 is an enlarged anterior-posterior sectional view similar to FIG. 23, but illustrating threaded retraction of an inner adjustment ring to relieve spring-loaded retention forces acting on the ball member, thereby facilitating return movement of the ball member to a normal operating position; and FIG. 25 is an enlarged anterior-posterior sectional view similar to FIG. 24, and depicting return displacement of the ball member to the normal operating position.

DETAILED DESCRIPTION OF THE PREFERRED EMBODIMENTS

Figure 1:
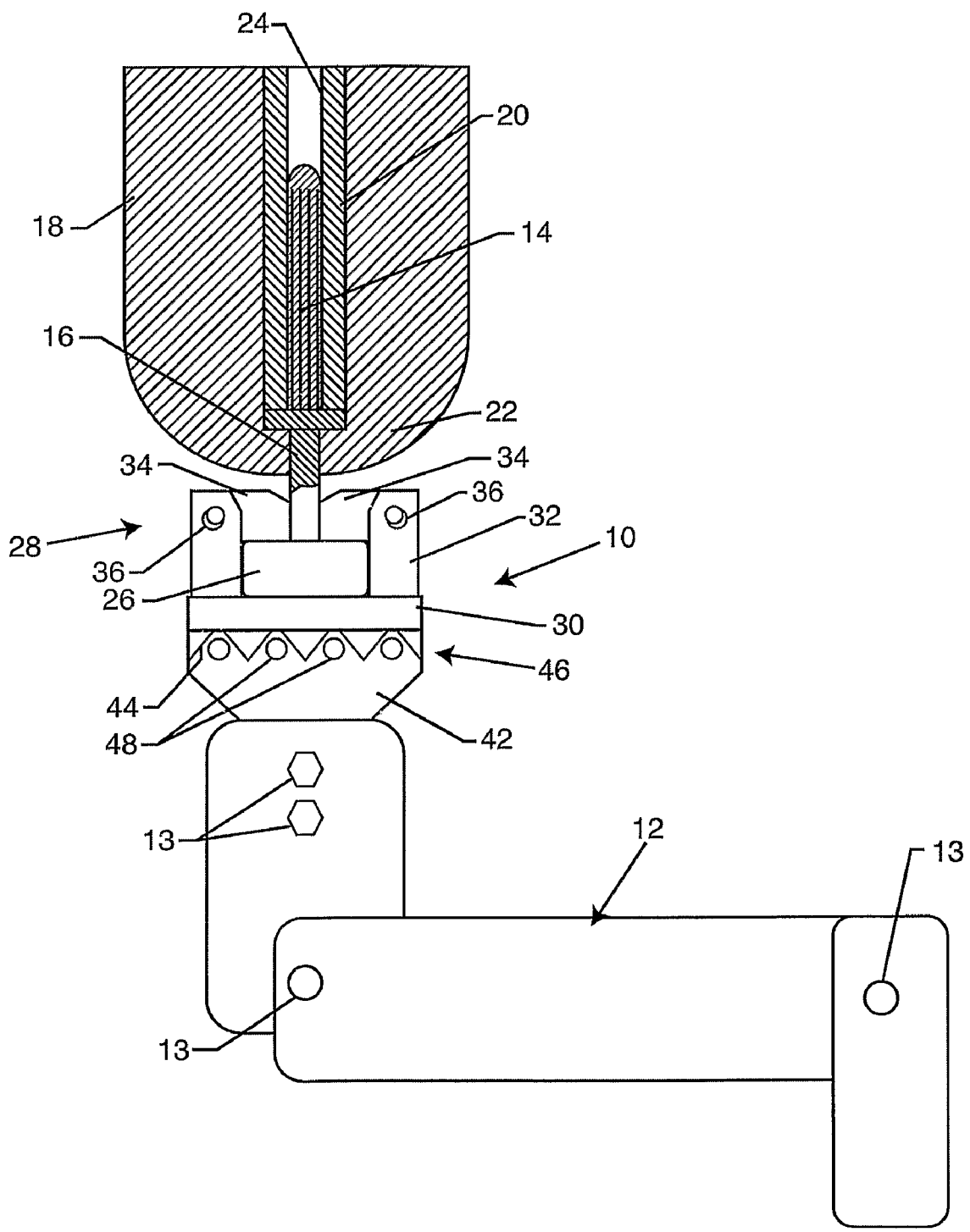
FIG. 1 is a somewhat schematic diagram showing the releasable attachment system of the present invention in combination with a bone anchored prosthesis mounting post for use in releasable external attachment to an exoskeletal prosthesis.

As shown in the exemplary drawings, an attachment system referred to generally by the reference numeral 10 in FIGS. 1 and 5-10 is provided for releasably connecting an external or exoskeletal prosthesis 12 in a bone anchored mounting system of the type having an implanted bone anchored mounting post 14. The attachment system 10 is designed for secure and stable attachment of the bone anchored mounting post 14 to the external prosthesis 12, such as a prosthetic limb or the like for an amputee. In accordance with the invention, the attachment system 10 includes a safety release means or mechanism which provides a substantially rigid and direct-coupled attachment of the prosthesis 12 to an externally protruding fixator structure 16 formed on or carried by the implanted mounting post 14, to accommodate a substantially normal range of force loads encountered during substantially normal movement and/or use of the prosthesis 12. However, the safety release mechanism is also designed for displacement and ultimately for breakaway separation in response to an applied force load exceeding a predetermined design limit, thereby safeguarding the prosthesis and the bone-mounting post attachment interface against undesired fracture failure.

Figure 2:
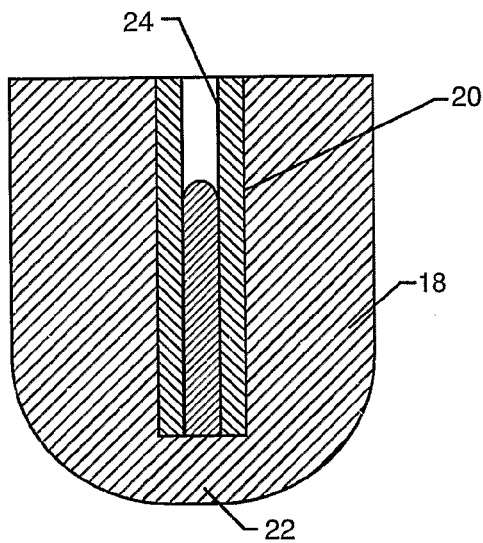
FIG. 2 is a somewhat schematic diagram illustrating an amputated upper leg portion of a transfemoral amputee, prior to implanted installation of a bone anchored mounting post.

The releasable attachment system 10 of the present invention is particularly designed for use with external or exoskeletal prosthetic fixation or mounting systems of the type having the internal, implanted bone anchored mounting post 14 which is surgically attached to and securely supported by patient bone, as by means of osseointegration or the like. For example, with reference to FIGS. 2-4, an amputated patient limb 18 such as the upper leg in the case of a transfemoral amputee includes a portion of a long patient bone 20 such as the femur which, prior to amputation, anatomically supports a range of loads encountered during normal ambulatory movements. When amputated, as viewed in FIG. 2, the femur 20 is surgically severed, and upon healing is covered by soft stump tissue 22 including skin and the like.

Figure 3:
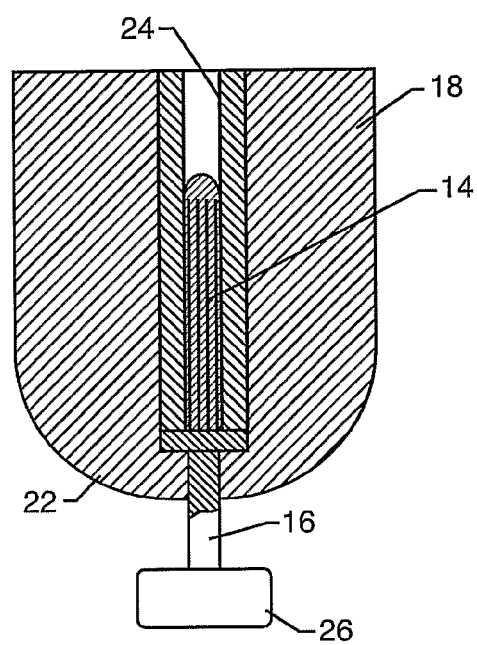
FIG. 3 is a somewhat schematic diagram similar to FIG. 2, but showing the amputated upper leg portion following implantation of the bone anchored mounting post.
Figure 4:
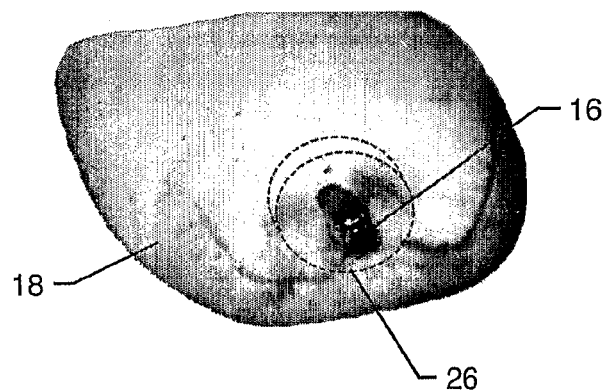
FIG. 4 is a fragmented perspective view showing the lower or stump end of the amputated upper leg portion, and illustrating a fixator structure protruding externally from the amputated limb.
Figure 5:
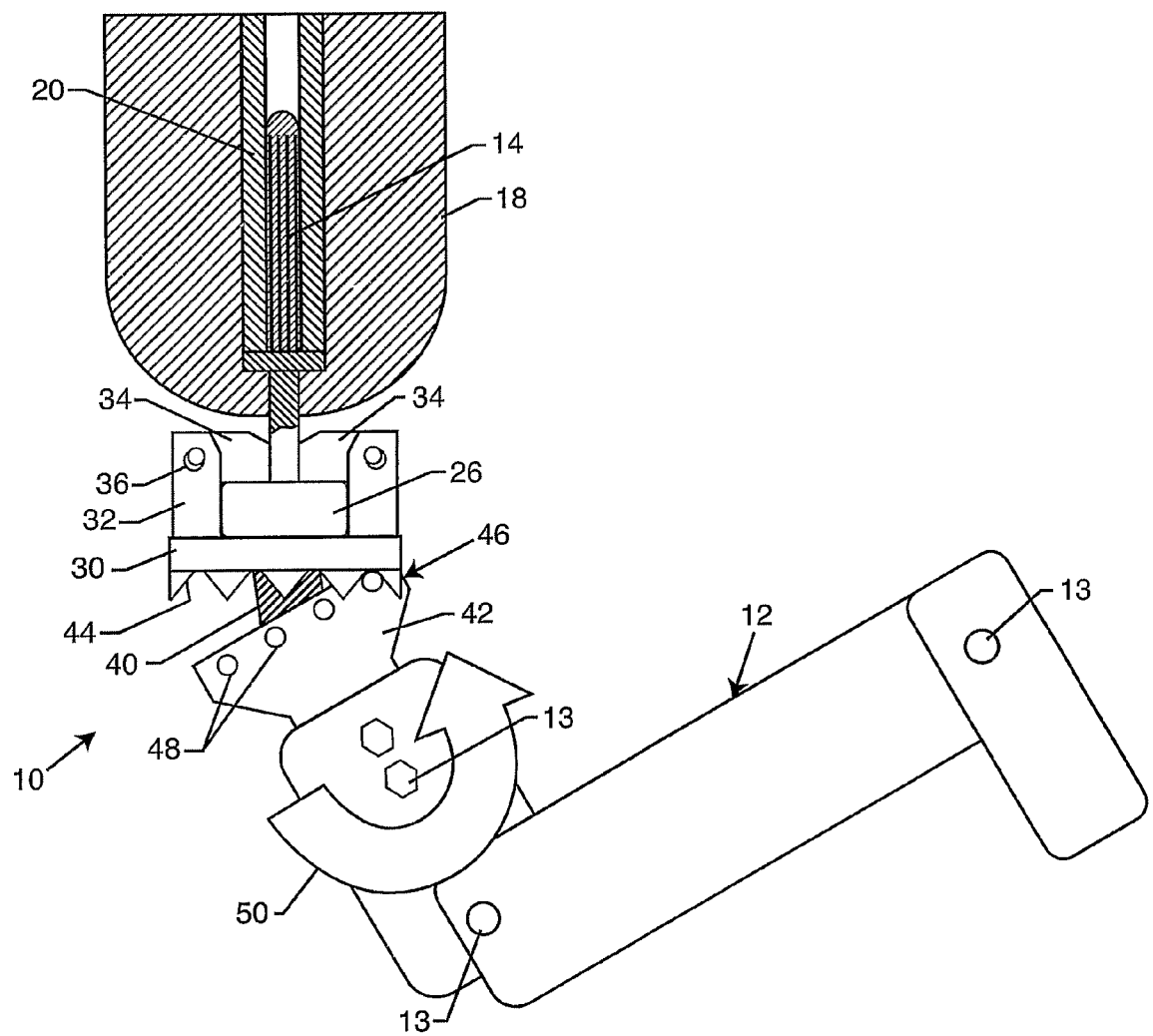
FIG. 5 is a somewhat schematic diagram similar to FIG. 1, but depicting initial release and displacement of the attachment system in response to a bending force overload condition.

FIG. 3 shows the bone anchored mounting post 14 in the form of an elongated tube or rod constructed typically from a high strength and biocompatible metal or the like and adapted for secure affixation within the intramedullary canal 24 of the long patient bone 20. In this regard, mounting post affixation can be obtained by a threaded post construction (not shown) adapted for thread-in placement into the medullary canal 24, or by alternative affixation means (also not shown) such as press-fitting, and/or by the provision of a bone ingrowth surface or surfaces on the mounting post 14. The fixator structure 16 comprises an elongated post or pin carried by or formed integrally with the implanted bone anchored mounting post 14, and protrudes therefrom through the overlying soft stump tissue 22 to an externally positioned lower or distal end. As shown in FIGS. 3-4, the lower or distal end of the fixator structure 16 includes or carries a mounting element 26 such as the illustrative radially enlarged mounting flange for releasable connection to the prosthesis 12. This releasable connection is provided by the attachment system 10 of the present invention.

FIG. 1 shows the attachment system 10 in accordance with one preferred form of the invention. As shown, the system 10 including the safety release mechanism comprises a first component in the form of an upper socket member 28 for spring-loaded clamp-on and substantially snap-fit releasable reception and retention of the mounting flange 26 on the fixator structure 16. This upper socket member 28 comprises a generally cup-shaped structure having a sturdy and rigid base plate 30 in combination with an upstanding sturdy and rigid peripheral wall 32 which cooperates with the base plate 30 to define an upwardly open, generally cup-shaped receptacle. A plurality of at least two jaw elements 34 are pivotally mounted at or near an upper margin of the peripheral wall 32 in a radially inwardly projecting orientation. Springs 36 urge these jaw elements 34 toward a normal position pivoted downwardly relative to the peripheral wall 32.

With this construction, the spring-loaded jaw elements 36 cooperate with the base wall 30 and associated peripheral wall 32 to define a pocket 38 (FIG. 8) having a size and shape for clamped, substantially snap-fit reception of the mounting flange 26 on the fixator structure 16. The downwardly loaded jaw elements 36 springably support and retain the mating flange 26 in an essentially fixed position relative to the socket member 28, throughout a normal range of mechanical loads. However, as will be described in more detail, the spring-loaded jaw elements 36 are designed to accommodate movement of the mounting flange 26 relative to the socket member 28 when a force overload condition occurs.

A relatively short tension member or tension band 40 (shown in FIG. 5) is suitably connected to the underside of the socket member base plate 30, and extends downwardly therefrom for suitable connection to an upper face of a lower base link 42. This lower base link 42 comprises a second component and is shown connected to the prosthesis 12 which may include one or more mechanical links secured to each other by appropriate fasteners 13 or the like. A plurality of radially outwardly and downwardly open detent seats 44 are defined between a sawtooth array 46 protruding downwardly from the underside of the base plate 30. A corresponding plurality of radially projecting detent pins 48 are carried by or formed on the lower base link 42 for respective seated engagement within the detent seats 44 of the sawtooth array 46. In a normal position, the tension band 40 (which may be formed from a strong and longitudinally resilient material such as metals, plastics, wood and composites) draws the lower base link 42 upwardly for secure and stable, substantially rigid seated engagement of the detent pins 48 within the sawtooth detent seats 44. However, and as will be described herein in more detail, the tension band 40 accommodates relative movement between the upper socket member 28 and the lower base link 42 when a force overload condition occurs.

FIGS. 5-8 illustrate safety release operation of the attachment system 10 in response to a bending force overload condition, wherein a bending force illustrated by arrow 50 is encountered with a magnitude exceeding a predetermined maximum limit. Upon such bending force overload, the tension band 40 in initially stretched (FIG. 5) to accommodate pivoting motion of the lower base link 42 away from the sawtooth array 46 at the underside of the upper socket member 28. Accordingly, in the presence of a relatively minor bending force overload, the tension band 40 springably or elastically permits a limited amount of relative movement between the socket member 28 and base link 42 to protect the prosthetic components including the attachment interface of the implanted mounting post 14 with patient bone 20 against risk of fracture failure.

Figure 6:
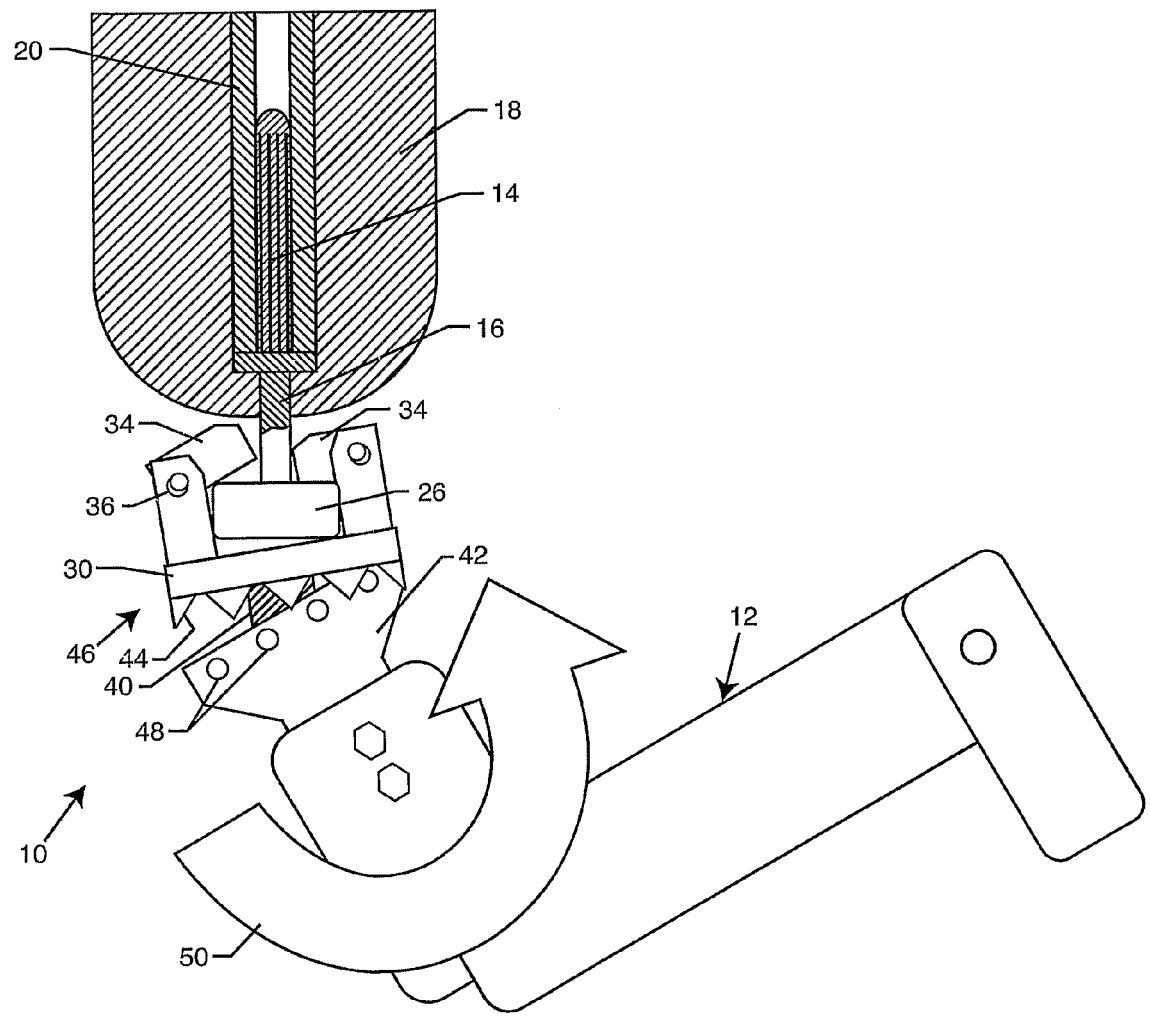
FIGS. 6 through 8 are diagrams similar to FIG. 5, and showing successively further release and displacement of the attachment system in response to a bending force overload condition.
Figure 7:
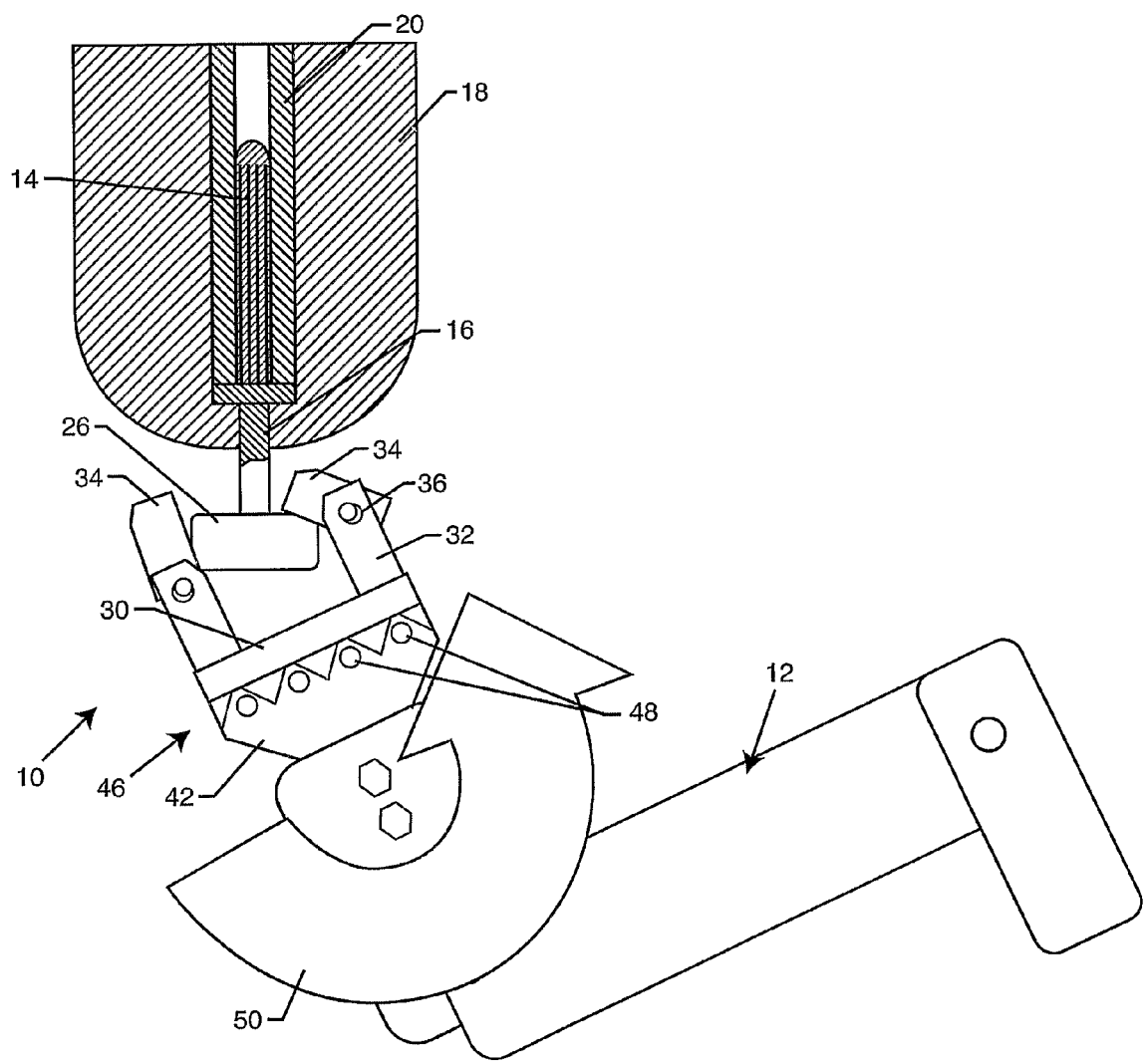
Figure 8:
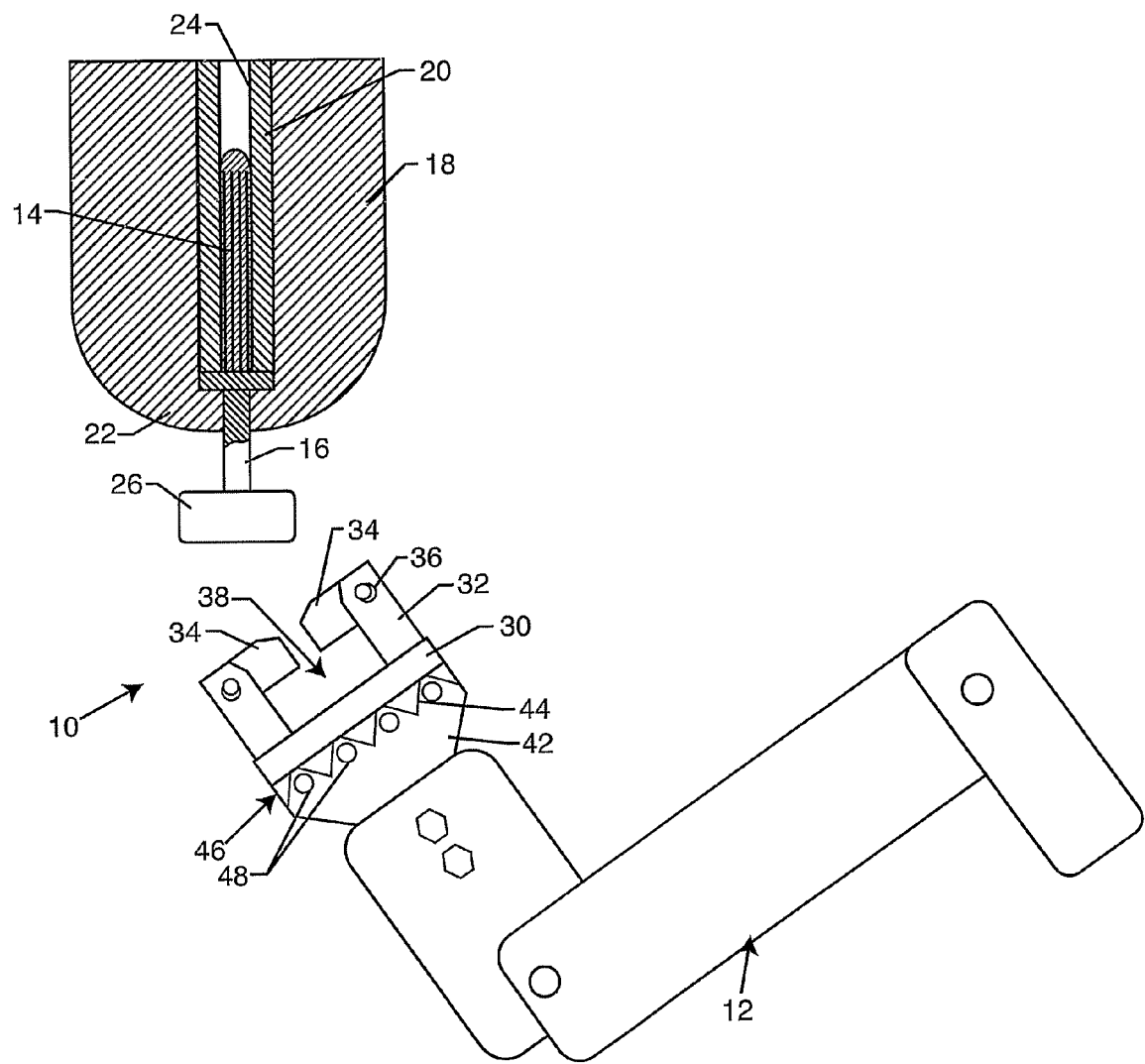

Upon encountering a larger magnitude bending force overload, as viewed in FIG. 6, the spring-loaded jaw elements 36 are designed to displace. That is, the mounting flange 26 at the lower end of the fixator structure 16 bears against the underside surfaces of the jaw elements 36 and forces them to pivot upwardly in a manner permitting limited relative movement therebetween. If the bending force overload condition is severe enough, the jaw elements 36 will continue to pivot upwardly as viewed in FIG. 7 to accommodate complete release or separation of the socket member 28 from the mounting flange 26 (FIG. 8). Such socket member separation is, of course, accompanied by complete release or separation of the prosthesis 12 from the amputated limb 18. While such prosthesis separation renders the prosthesis temporarily ineffective (until re-attached to the fixator structure 16) and may cause the patient to fall, e.g., when the prosthesis comprises an artificial leg, the prosthetic components and the patient bone 20 are protected against fracture failure.

Figure 9:
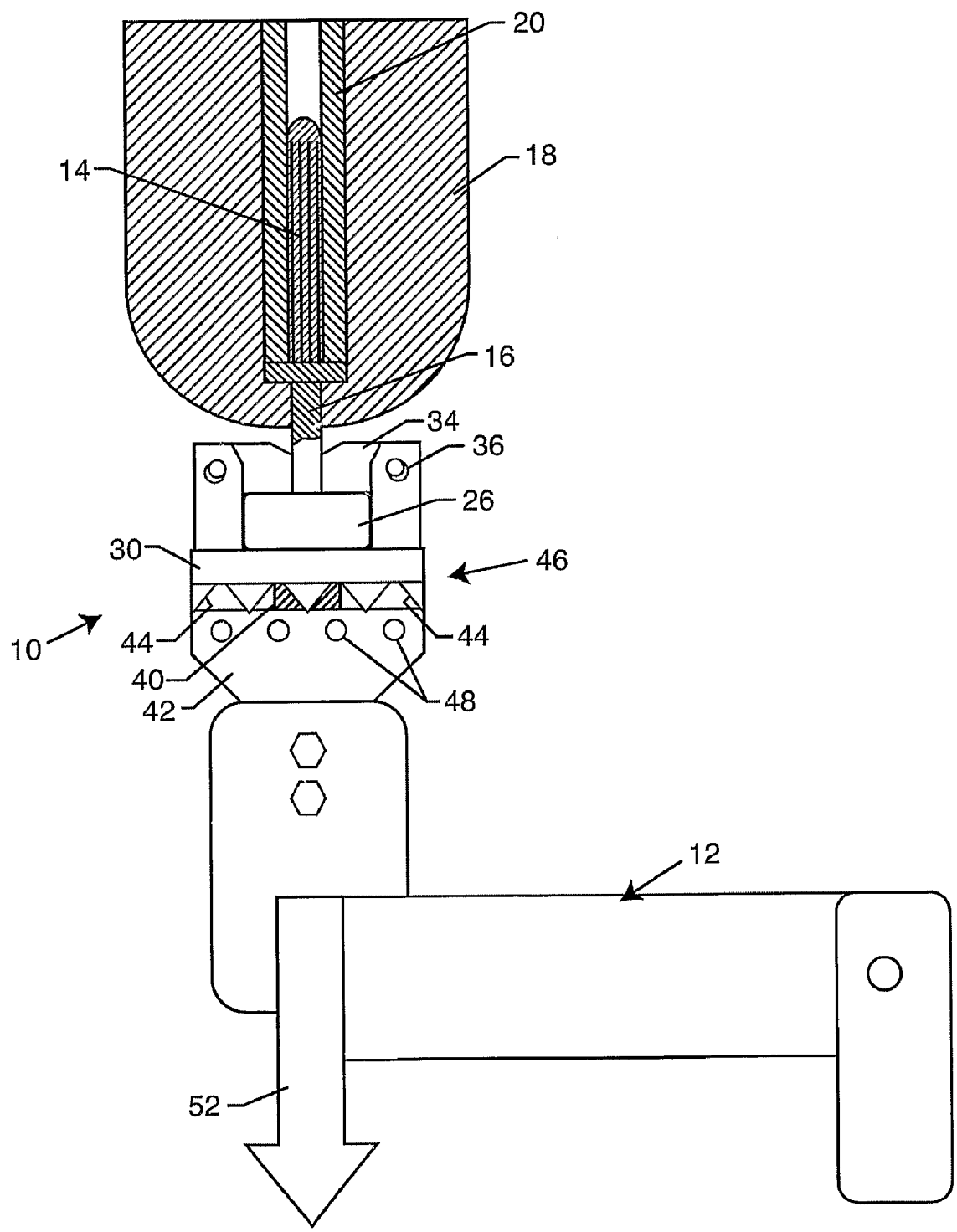
FIG. 9 is another schematic diagram similar to FIGS. 1 and 5-8, illustrating initial release and displacement of the attachment system in response to a tensile force overload condition.

FIG. 9 shows response of the attachment system 10 to a tensile force overload acting in the direction of arrow 52. In particular, upon encountering a tension force overload, the tension band 40 elongates to accommodate relative motion between the upper socket member 28 and the lower base link 42. In the event of a tension overload of substantial degree, further downward force on the tension band 40 will eventually exceed the retention force applied to the fixture structure mounting flange 26 by the spring-loaded jaw elements 36, resulting in separation and release of the mounting flange 26 from the socket member 28 as depicted generally in FIG. 8. Once again, such component separation beneficially protects the prosthesis components and the patient bone 20 against fracture failure.

Figure 10:
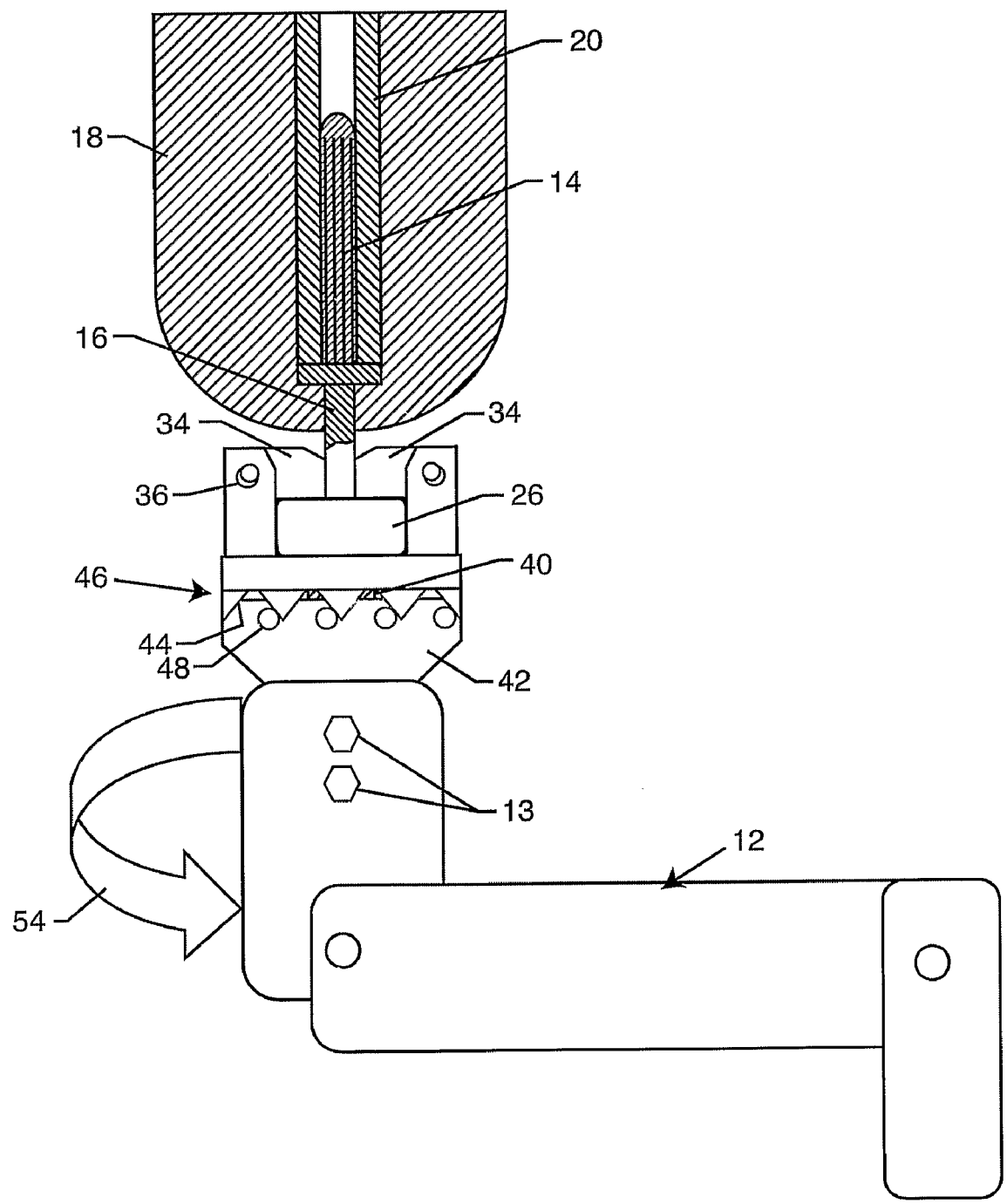
FIG. 10 is a somewhat schematic diagram similar to FIGS. 1 and 5-9, and showing initial release and displacement of the attachment system in response to a torsion force overload condition.
Figure 11:
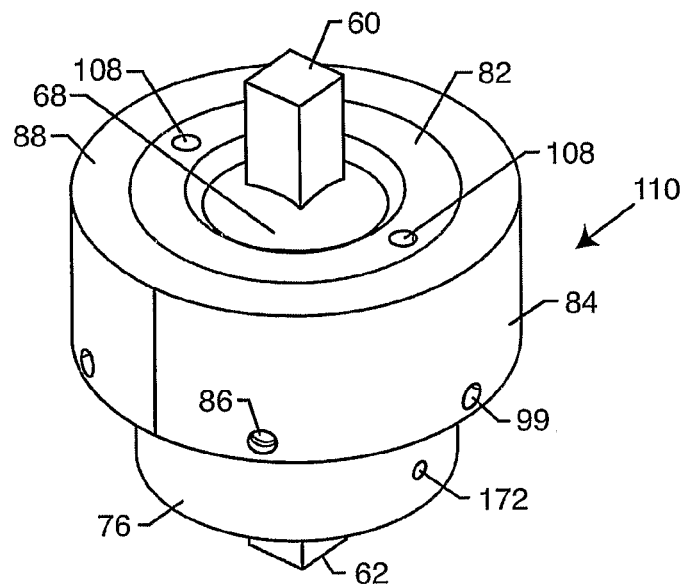
FIG. 11 is a perspective view showing the top, front and left sides of a releasable attachment unit constructed in accordance with one alternative preferred form of the invention.

FIG. 10 illustrates response of the attachment system 10 to a torsion force overload condition represented by arrow 54. As shown, in the event of torsion force overload, the detent pins 48 on the lower base link 42 ride downwardly within the individual detent seats 44 defined by the sawtooth array 46, for accommodating rotation of the lower base link 42 relative to the sawtooth array in the direction of the applied torque. The tension band 40 stretch-elongates sufficiently to accommodate this relative rotation, and then draws the detent pins 48 back upwardly into adjacent seats 44 defined by the sawtooth array. Accordingly, the sawtooth array 46 cooperates with the detent pins 48 and the tension band 40 to provide a spring-loaded torsion clutch that accommodates relative rotation in either direction upon encountering a torsion force overload.

In actual use, forces applied to the prosthesis 12 and the related attachment system 10 typically comprise a combination of bending, tensile, and/or torsion forces. The attachment system 10 of the present invention responds cooperatively to these applied forces to provide a sturdy and essentially rigid interconnection between the prosthesis 12 and patient bone 20, provided that these forces do not exceed a predetermined safe design limit in any direction. If and when the applied forces do exceed such predetermined safe design limit in any or in a combination of directions, the attachment system 10 responds to permit an appropriate degree of relative movement between components sufficient to prevent fracture failures. If the applied force overload is sufficiently high, the permitted relative movement involves separation of the prosthesis from the fixator structure 16 of the bone anchored mounting post 14.

Figure 12:
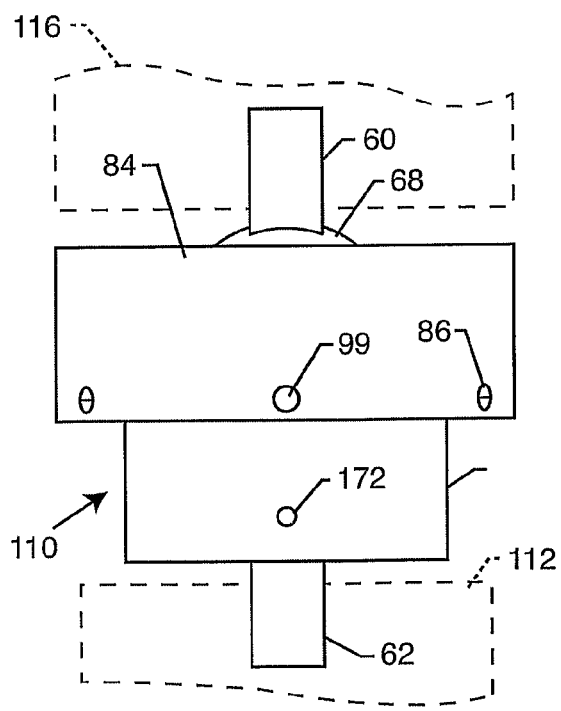
FIG. 12 is a front elevation view of the releasable attachment unit of FIG. 11.
Figure 13:
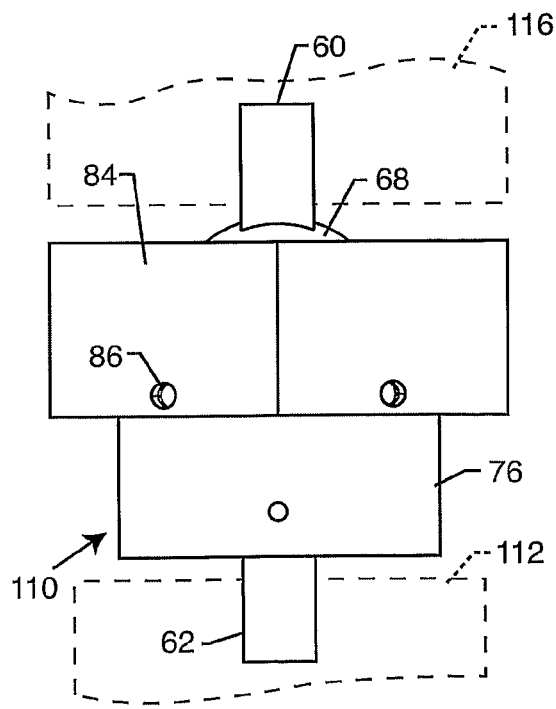
FIG. 13 is a left side elevation view of the releasable attachment unit of FIG. 11.
Figure 14:
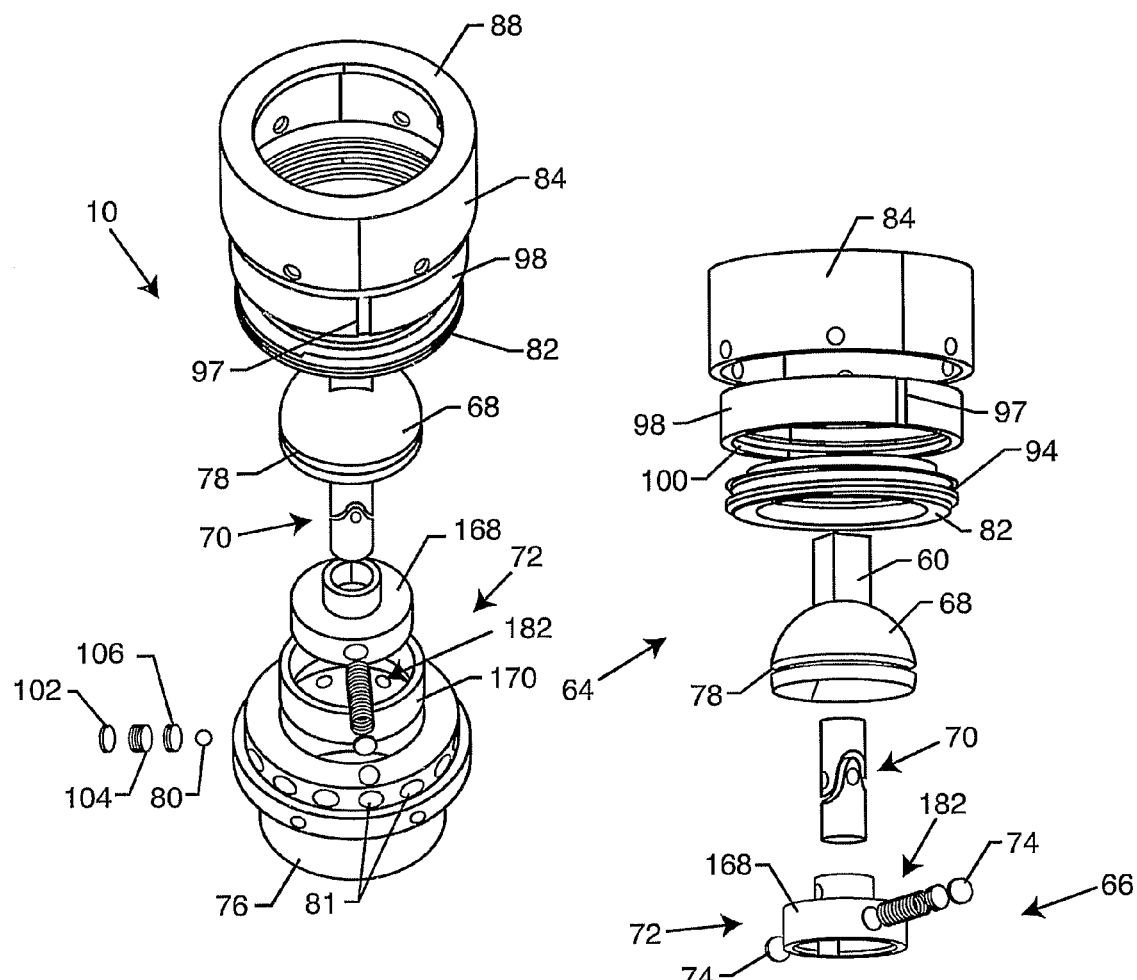
FIG. 14 is an exploded top perspective view of the releasable attachment unit of FIG. 11.
Figure 15:
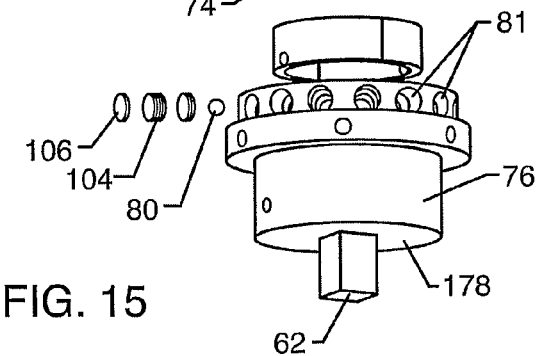
FIG. 15 is an exploded bottom perspective view of the releasable attachment unit of FIG. 11.
Figure 16:
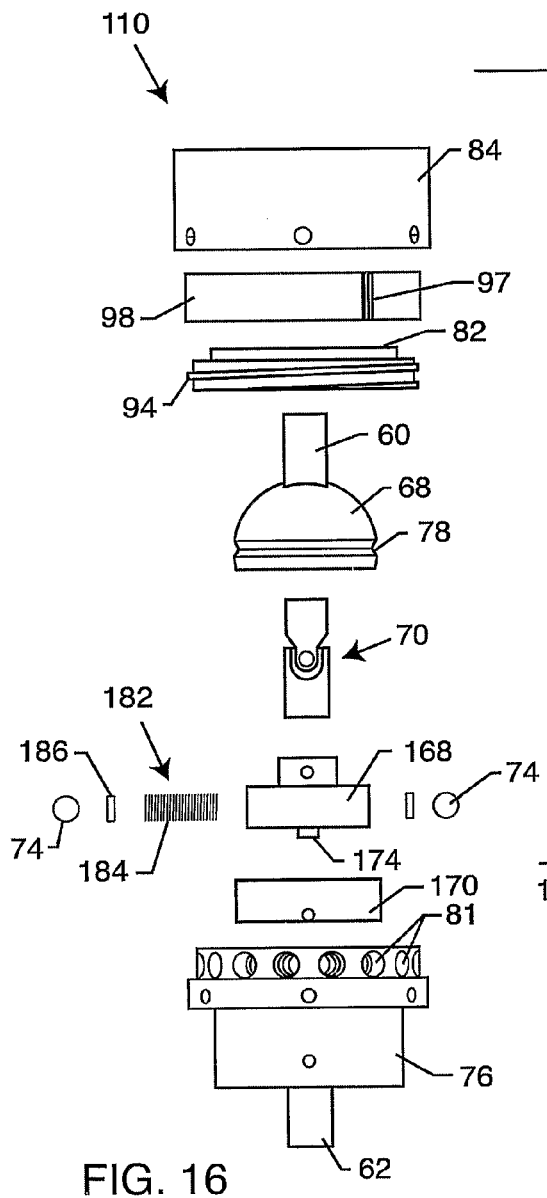
FIG. 16 is an exploded front view of the releasable attachment unit of FIG. 11.
Figure 17:
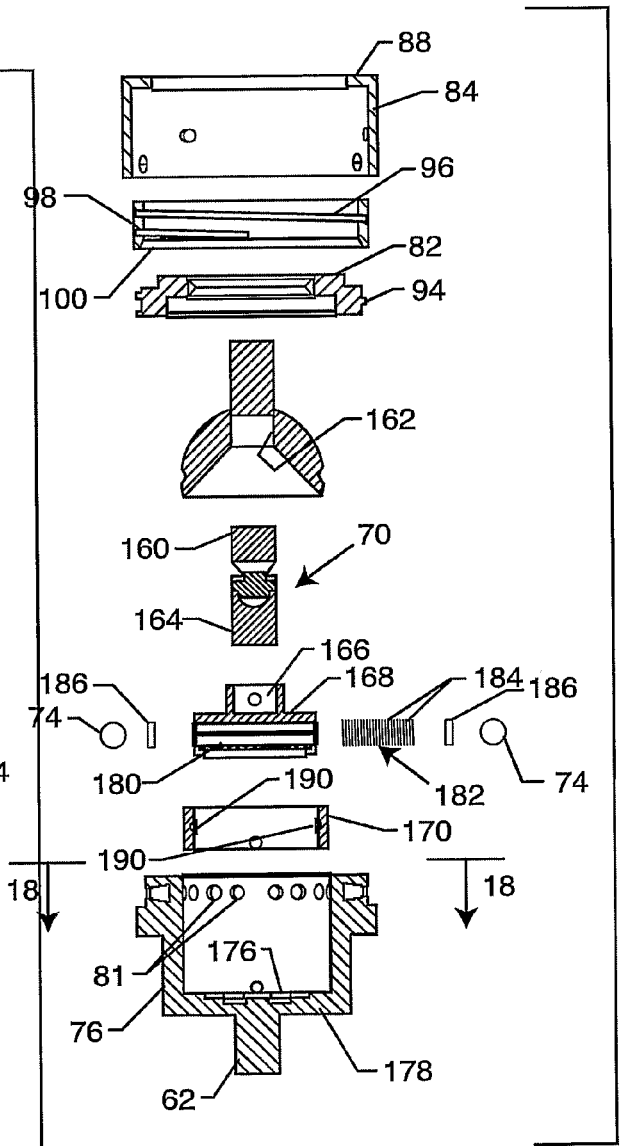
FIG. 17 is an exploded saggital or medial-lateral sectional view of the releasable attachment unit shown in FIG. 16.
Figure 18:
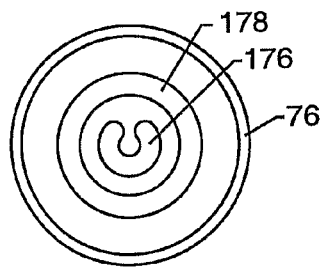
FIG. 18 is an enlarged top plan view of a cup-shaped housing forming a portion of the releasable attachment unit, taken generally on the line 18-18 of FIG. 17.
Figure 19:
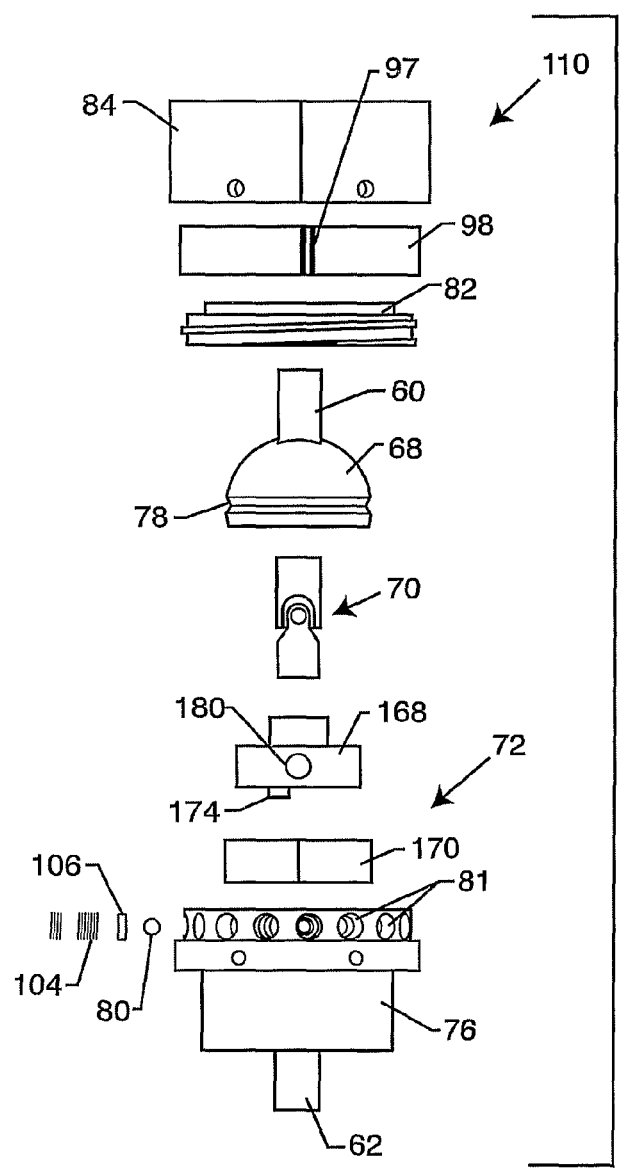
FIG. 19 is an exploded left side elevation view of the releasable attachment unit of FIG. 11.
Figure 20:
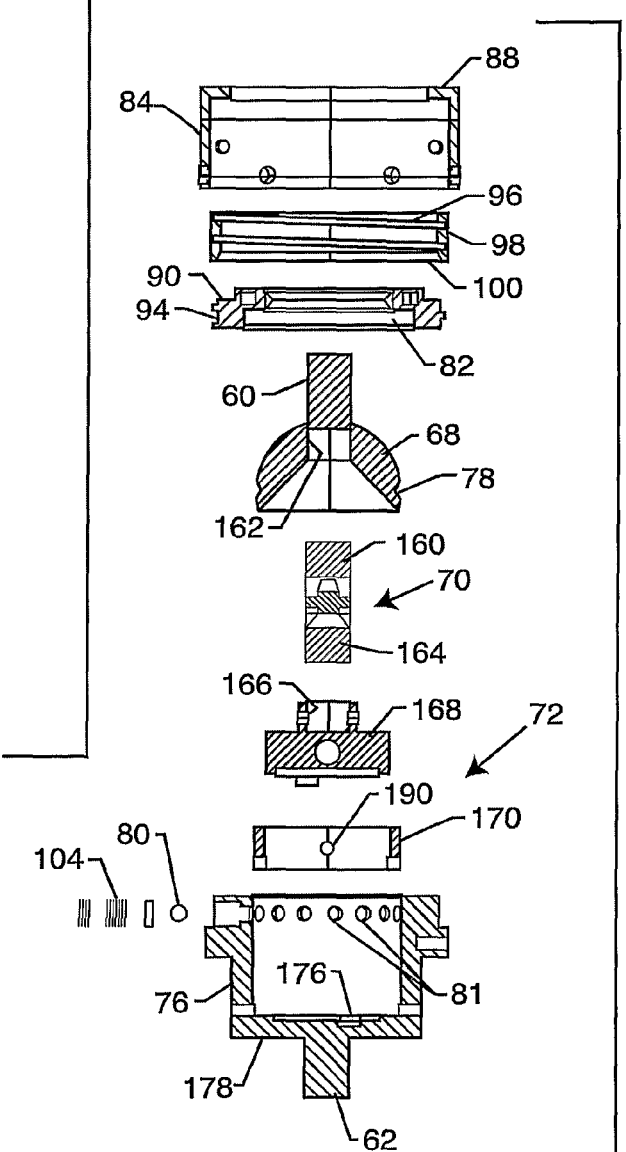
FIG. 20 is an exploded anterior-posterior sectional view of the releasable attachment unit shown in FIG. 19.
Figure 21:
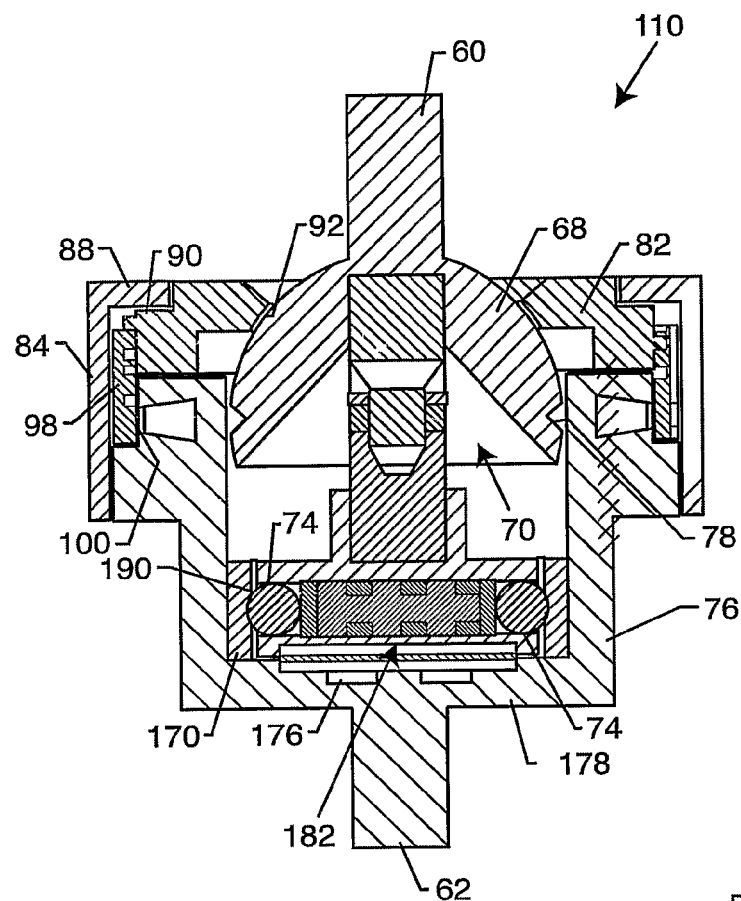
FIG. 21 is an enlarged saggital or medial-lateral sectional view of the assembled releasable attachment unit shown in FIG. 17.

FIGS. 11-25 depict an alternative preferred form of the invention, wherein a modified releasable attachment unit 110 is provided for connection between an external fixator structure 116 (FIGS. 12-13) formed on or carried by a bone anchored mounting post (not shown) or the like and an exoskeletal prosthesis 112 such as a prosthetic limb. This modified releasable attachment unit 110 includes a first component in the form of an upwardly projecting mounting stud 60 having a non-circular cross sectional shape such as the illustrative square cross section for quick and easy attachment to the fixator structure 116 in any suitable manner, as by means of one or more set screws (not shown). Similarly, the attachment unit 110 further includes a second component in the form of a downwardly projecting mounting stud 62 which also has a non-circular cross sectional shape such as the illustrative square shape for quick and easy attachment in a secure and stable manner to the prosthesis 112, as by means of one or more set screws (also not shown).

In operation, the releasable attachment unit 110 normally provides a rigid, substantially motion-free interface connection between the fixator structure 116 and the prosthesis 112 for normal patient movements, such as normal walking movements in the case of a prosthetic leg. However, upon encountering a force overload condition attributable, for example, to an excessive bending force or an excessive torsion force, the attachment unit 110 is designed to release quickly and substantially completely to prevent transmission of said excessive force via the fixator structure 116 to the patient bone. Accordingly, the releasable attachment unit 110 comprises a safety release mechanism of alternative design for safeguarding against highly undesirable fracture failures.

In general terms, the modified releasable attachment unit 110 comprises an upper bending force clutch 64 for adjustably responding to a bending force overload condition, and a lower torsion force clutch 66 for adjustably responding to a torsion force overload condition. The upper clutch 64 includes a relatively large ball member 68 having the upwardly projecting mounting stud 60 carried thereon as by integral formation therewith. This ball member 68 is coupled by means of a universal joint linkage 70 with the lower torsion force clutch comprising an underlying torque cartridge 72 including spring-loaded detent balls 74. The ball member 68 and the torque cartridge 72 are carried within a lower, generally cup-shaped unit housing 76. The downwardly projecting mounting stud 62 is carried on the underside of this housing 76 as by integral formation thereon.

More specifically, the ball member 68 comprises a relatively large part-spherical or ball-shaped component of generally hemispherical configuration. The ball member 68 has a diametric size for slide-fit reception into the upwardly open unit housing 76, as viewed best in FIGS. 21-25. In this position, the upper mounting stud 60 projects upwardly from the ball member 68. In a normal operating position, the ball member 68 is oriented within the unit housing 76 so that the upper mounting stud 60 projects generally coaxially with respect to the unit housing 76 (FIGS. 21-22 and 25), for suitable connection of the stud 60 to the fixator structure 116 (FIGS. 12-13) as previously described.

A peripheral groove 78 is formed in the ball member 68 generally near a lower margin thereof, for spring-loaded partial reception of a circumferential array of clutch balls 80 carried within a respective plurality of radially outwardly open ports 81 formed in the housing 76 near the open upper end thereof. Each clutch ball 80 is adapted for radially inward biasing with a selected spring force for partial reception into the ball member groove 78, for purposes of releasably locking the ball member 68 in the upright normal operating position. Importantly, the spring locking force is adjustably selectable for custom setting of a release force or release point in response to a bending force exceeding a predetermined selected threshold value. When the unit 110 is subjected to a bending release force exceeding the selected set point, the clutch balls 80 retract radially outwardly from the ball member groove 78 sufficiently to permit ball rotation or displacement from the normally locked operating position to an unlocked angular position as viewed in FIGS. 23-24.

The spring locking/release force is adjustably set by means of an inner adjustment ring 82 rotatably carried within a generally annular cover 84 fastened onto the upper end of the unit housing 76 as by means of a plurality of short screws 86 or the like. This annular cover 84 has a radially in-turned upper flange 88 which overlies and engages an annular shoulder 90 on the inner adjustment ring 82 to retain said ring 82 in a position with an inner diameter surface 92 thereof pressed against the part-spherical outer surface of the ball member 68.

The inner adjustment ring 82 has an externally threaded segment 94 engaged with an internally threaded segment 96 of an outer adjustment ring 98. This internally threaded segment 96 of the outer adjustment ring 98 merges with a tapered-edge bearing seat 100 positioned for bearing against an outboard spacer 102 of a clutch spring assembly including a disk spring 104 or the like interposed between the outboard spacer 102 and an inboard spacer 106 engaged in turn with an associated one of the clutch balls 80.

Rotation of the inner adjustment ring 82, as by means of engagement of a pair of upwardly open drive ports 108 (FIG. 1) by a spanner wrench (not shown) or the like, causes upward or downward translation of the outer adjustment ring 98, in accordance with the direction of rotational displacement. In this regard, the outer adjustment ring 98 has as least one axially or vertically elongated slot 97 formed therein for slide-guided reception of an associated set screw 99 on the cover 84 to limit the outer adjustment ring 98 to axial or up/down displacement in response to rotation of the inner adjustment ring 82. Downward displacement of the outer adjustment ring 98 moves the tapered-edge bearing seat 100 thereon into progressively further radially overlying engagement with the outboard spacers 102 of the clutch spring assemblies, and thereby progressively increases the inward spring force applied to the associated clutch balls 80. Accordingly, such downward displacement of the outer adjustment ring 98 is accompanied by increased inward spring force applied to the clutch balls 80, and thereby adjustably increases bending release force required to displace the ball member 68 from the upright normal operating position. However, as viewed in FIG. 23, when this adjustably set bending release force limit is reached, as represented by an adjustably set bending force overload condition, the clutch balls 80 retract radially outwardly from the ball member groove 78 sufficiently to permit rapid shifting of the ball member 68 to an angularly oriented release position.

Following such release in response to a bending force overload condition, the ball member 68 is returnable to the upright normal operating position in a manner that does not require application of substantial force or effort. In this regard, the inner adjustment ring 82 can be rotationally displaced to retract the outer adjustment ring 98 upwardly and thereby retract the tapered-edge bearing seat 100 upwardly relative to the clutch spring assemblies. This results in a substantial relieving of the spring forces urging the clutch balls 80 in a radially inwardly direction, and thereby permits relatively quick and easy return of the ball member 68 to the upright normal operating position. When this upright normal position is achieved, the inner adjustment ring 82 can be reverse-rotated in a manner increasing the bending force release point to the desired higher level, as previously described.

The universal joint linkage 70 interconnects the ball member 68 with the lower torsion force clutch 66 mounted within a lower end of the cup-shaped unit housing 76. In this regard, the U-joint linkage comprises an upper drive member 160 of non-circular cross sectional shape, such as a square-drive key or the like, seated within a matingly shaped socket 162 formed within a hollow underside of the ball member 68. The U-joint linkage 70 additionally includes a lower drive member 164 which is also formed with a non-circular shape, such as a square-drive key or the like, seated within a matingly shaped socket 166 formed on the upper side of a torque member or torque plate 168. These upper and lower drive members 160 and 164 of the U-joint linkage 70 are rotatably interconnected as by means of a pair of pivotally joined link components conventionally provided in a so-called universal joint. Accordingly, further description of U-joint construction details are not included herein, such details being known to persons skilled in the art. One preferred and exemplary U-joint linkage is available from Lovejoy, Inc., of Downers Grove, Ill., under the product designation D-2 Solid U-Joint.

Figure 22:
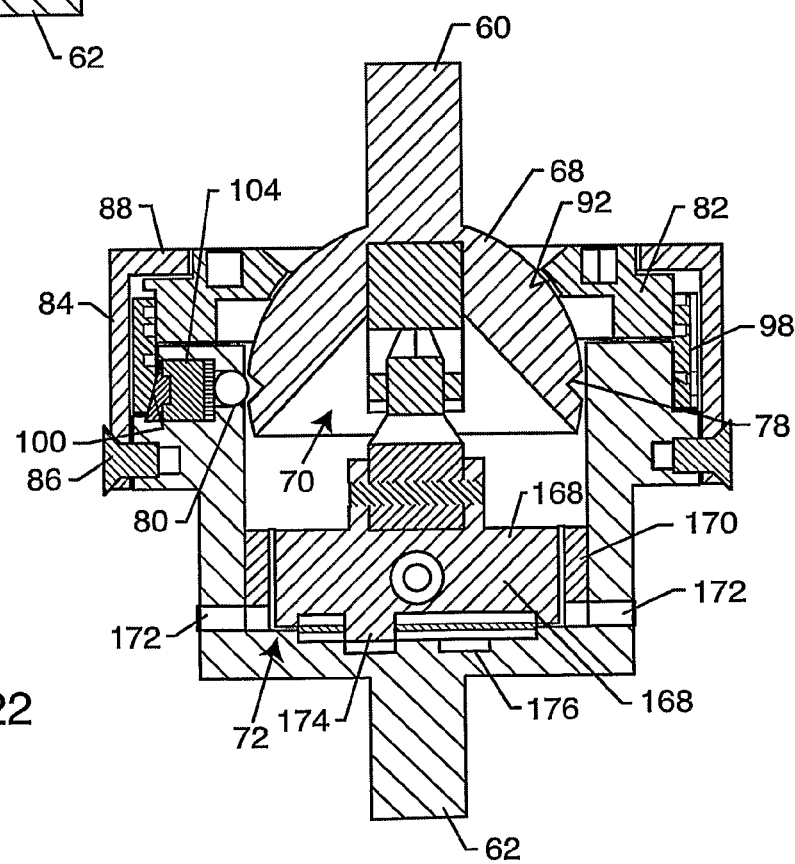
FIG. 22 is an enlarged anterior-posterior sectional view of the assembled releasable attachment unit shown in FIG. 20.

The torque plate 168 comprises a portion of the torque cartridge 72, and has a generally disk-shaped profile sized for slide-fit reception into a cylindrical lower region of the cup-shaped unit housing 76, preferably within an annular torque or spacer ring 170 which is slidably seated in turn within the housing 76 and locked against rotation therein as by radially extending set pins 172 (FIG. 22). The torque plate 168 is diametrically sized for relatively free rotation within the torque spacer ring 170, and includes an axially downwardly projecting tab 174 extending into a part-annular channel 176 formed in a base wall 178 of the unit housing 76. As shown best in FIG. 18, this part-annular channel 176 extends on a common radius through an arcuate length dimension of less than 360°, such as an arcuate length on the order of about 340-350°.

A diametrically extending bore 180 is formed in the body of the torque plate 168. This bore 180 is sized and shaped to receive and support a spring unit 182 including, e.g., a set of disk springs 184 sandwiched between a pair of spacers 186. The spacers 186 bear in turn against a pair of detent balls 74 to urge those balls 74 radially outwardly beyond the perimeter of the torque plate 168 with a predetermined force setting. As shown best in FIG. 21, the detent balls 74 are urged radially outwardly into a matingly shaped and diametrically aligned pair of shallow detent seats 190 formed in the inner diameter surface of the torque spacer ring 170. Accordingly, the spring unit 182 normally engages and locks with the torque spacer ring 170 for releasably maintaining the torque plate 168 in a predetermined rotational position relative to the torque spacer ring 170 and the associated unit housing 76. In this normally locked and normal operating position, the tab 174 on the torque plate 168 is positioned within the underlying channel 176 generally mid-way between the opposed channel ends.

Upon encountering a torsion force overload condition, wherein the applied torsion force exceeds the spring forces holding the detent balls 74 within the detent seats 190, the detent balls 74 retract against the springs 184 sufficiently to permit relative rotation between the torque plate 168 and the torque spacer ring 170 within the unit housing 76. Such relative rotation corresponds with safety release of the attachment unit 110 to prevent undesired fracture failure. The prosthesis 112 is thus permitted to rotate with the housing 76, relative to the torque plate 168 and ball member 68 coupled thereto wherein the ball member 68 is coupled in turn to the patient bone interface. Importantly, the tab 174 accommodates such rotation through an angular increment of nearly but less than 180°, such as an increment of about 160°. Such rotational increment is normally sufficient to relieve the torsion force overload, and also precludes re-engagement of the detent balls 74 with the opposed detent seats 190. Accordingly, with the detent balls 74 disengaged from the detent seats 190, the unit 110 can be returned quickly and easily to the desired normal operating position by merely back-rotating the prosthesis 112 and/or housing 76 until the detent balls 74 re-engage in a snap-fit manner with the associated detent seats 190.

Accordingly, the attachment unit 110 provides a safety release mechanism for securely interconnecting the prosthesis 112 with the associated bone-supported fixator structure 116 in a substantially motion-free secure and stable manner during normal operating conditions. However, upon encountering a bending force overload condition, or a torsion force overload condition, or a combination thereof, the attachment unit 110 provides the requisite safety release mechanism for quickly and substantially completely de-coupling in a manner to safeguard the bone-supported interface against fracture failures. Following a force overload incident, the attachment unit 110 can be returned quickly and easily to a normal operation position for resumed patient use.

Although various embodiments and alternatives have been described in detail for purposes of illustration, various further modifications may be made without departing from the scope and spirit of the invention. For example, persons skilled in the art will recognize and appreciate that the safety release mechanism as shown and described herein may be constructed in alternative configurations adapted to accommodate relative component movements in response to force overloads applied in different directions. Accordingly, no limitation on the invention is intended by way of the foregoing description and accompanying drawings, except as set forth in the appended claims.

What is claimed is:

1. A releasable attachment system for coupling an exoskeletal prosthesis to a patient limb having a bone anchored mounting post with an external fixator structure, said releasable attachment system comprising:
   a first component adapted for connection to the fixator structure;
   a second component adapted for connection to the prosthesis; and
   a safety release mechanism normally retaining the prosthesis in a rigid substantially motion-free interconnected relation to the fixator structure, said safety release mechanism responding to a force overload condition to permit relative movement between the prosthesis and the fixator structure;
   said safety release mechanism comprising a bending force clutch responsive to a bending force overload condition to permit relative angular displacement of said second component relative to said first component, and a torsion force clutch responsive to a torsion force overload condition to permit relative rotational displacement of said second component relative to said first component
   wherein said bending force clutch comprises a ball member movably mounted within a unit housing, and spring-loaded detent means engageable between said unit housing and said ball member for releasably retaining said ball member in a normal position within said unit housing, said detent means responding to a bending force overload condition to permit angular displacement of said ball member relative to said unit housing.

2. The releasable attachment system of claim 1 wherein said first component is carried by said ball member, and wherein said second component is carried by said unit housing.

3. The releasable attachment system of claim 1 wherein said spring-loaded detent means comprises an array of detent balls, and spring means for urging said detent balls with a selected spring force into engagement with a peripheral groove formed in said ball member.

4. The releasable attachment system of claim 3 wherein said spring-loaded detent means further comprises adjustment means for adjustably setting a detent spring force applied to said detent balls by said spring means for releasably retaining said ball member in said normal position.

5. The releasable attachment system of claim 4 wherein said adjustment means comprises a rotatable adjustment ring carried by said unit housing.

6. The releasable attachment system of claim 1 wherein said torsion force clutch comprises a torque member rotatably mounted within said unit housing, and spring-loaded detent means reacting between said torque member and said unit housing for releasably retaining said torque member in a normal position fixed against rotation within said unit housing, said detent means responding to a torsion force overload condition to permit rotational displacement of said torque member relative to said unit housing.

7. The releasable attachment system of claim 6 wherein said torsion force clutch further includes means for preventing full revolution rotational displacement of said torque member relative to said unit housing.

8. The releasable attachment system of claim 7 wherein said unit housing has a generally cup-shaped configuration defining a base wall at one end thereof, said means for preventing full revolution displacement of said torque member relative to said unit housing comprising a part-annular channel formed in said base wall and a tab carried by said torque member and protruding into said channel, said tab being generally centered within said channel when said torque member is in said normal position.

9. The releasable attachment system of claim 6 further including a torque ring mounted within said unit housing and fixed against rotation therein, said detent means being engageable between said torque ring and said torque member.

10. A releasable attachment system for coupling an exoskeletal prosthesis to a patient limb having a bone anchored mounting post with an external fixator structure, said releasable attachment system comprising:
    a first component adapted for connection to the fixator structure;
    a second component adapted for connection to the prosthesis; and
    a safety release mechanism normally retaining the prosthesis in a rigid substantially motion-free interconnected relation to the fixator structure, said safety release mechanism responding to a force overload condition to permit relative movement between the prosthesis and the fixator structure;
    said safety release mechanism comprising a bending force clutch responsive to a bending force overload condition to permit relative angular displacement of said second component relative to said first component, a torsion force clutch responsive to a torsion force overload condition to permit relative rotational displacement of said second component relative to said first component, and a universal joint interconnecting said bending and torsion force clutches.

11. The releasable attachment system of claim 10 wherein said bending force clutch comprises a ball member movably mounted within a unit housing, and first spring-loaded detent means engageable between said unit housing and said ball member for releasably retaining said ball member in a normal position within said unit housing, said first detent means responding to a bending force overload condition to permit angular displacement of said ball member relative to said unit housing; and wherein said torsion force clutch comprises a torque member rotatably mounted within said unit housing, and second spring-loaded detent means reacting between said torque member and said unit housing for releasably retaining said torque member in a normal position fixed against rotation within said unit housing, said second detent means responding to a torsion force overload condition to permit rotational displacement of said torque member relative to said unit housing.

12. The releasable attachment system of claim 11 wherein said first component is carried by said ball member, and wherein said second component is carried by said unit housing.

13. The releasable attachment system of claim 10 wherein said bending force clutch further includes adjustment means for adjustably setting a spring force associated for releasably retaining said ball member in said normal position.

14. The releasable attachment system of claim 11 wherein said torsion force clutch further includes means for preventing full revolution rotational displacement of said torque member relative to said housing.

15. A releasable attachment system for coupling an exoskeletal prosthesis to a patient limb having a bone anchored mounting post with an external fixator structure, the releasable attachment system comprising:
   a safety release mechanism connectable to the prosthesis and the fixator structure, the safety release mechanism including
      a housing having a first mounting post connectable to one of the prosthesis and the fixator structure,
      a bending force clutch connectable to the housing and to the other one of the prosthesis and the fixator structure,
      a torsion force clutch connectable to the housing and the bending force clutch,
      the bending force clutch including
         a first member having a second mounting post connectable to the other one of the prosthesis and the fixator structure, the first member movably mounted within the housing, and
         first release means coupled between the first member and the housing and responsive to a bending force overload condition to permit relative angular displacement between the first member and the housing, the torsion force clutch including
         a torque member rotatably mounted within the housing, and
         second release means reacting between the torque member and the housing for responding to a torque overload condition to permit relative rotational displacement between the housing and the first member, and
      a universal joint interconnecting the first member of the bending force clutch and the torque member of the torsion force clutch.

16. The releasable attachment system of claim 15 wherein the first member of the bending force clutch comprises a ball member movably mounted within the housing, and further wherein the first release means comprises spring-loaded clutch ball means engageable between the housing and the ball member for releasably retaining the ball member in a normal position within the housing, the spring-loaded clutch ball means responding to a bending force overload condition to permit angular displacement of the ball member relative to the housing.

17. The releasable attachment system of claim 16 wherein the second mounting post is carried by the ball member, and wherein the first mounting post is carried by the housing.

18. The releasable attachment system of claim 16 wherein the spring-loaded clutch ball means comprises an array of detent balls, and spring means for urging the clutch balls with a selected spring force into engagement with a peripheral groove formed in the ball member.

19. The releasable attachment system of claim 18 wherein the spring-loaded clutch ball means further comprises adjustment means for adjustably setting a spring force applied to the clutch balls by the spring means for releasibly retaining the ball member in the normal position.

20. The releasable attachment system of claim 16 wherein the second release means comprises spring-loaded detent means reacting between the torque member and the housing for releasably retaining the torque member in a normal position fixed against rotation within the housing, the detent means responding to a torsion force overload condition to permit rotational displacement of the torque member relative to the housing.

21. The releasable attachment system of claim 20 wherein the torsion force clutch further includes means for preventing full revolution rotational displacement of the torque member relative to the housing.

22. The releasable attachment system of claim 21 wherein the housing has a generally cup-shaped configuration defining a base wall at one end thereof, the means for preventing full revolution displacement of the torque member relative to the housing comprising a part-annular channel formed in the base wall and a tab carried by the torque member and protruding into the channel, the tab being generally centered within the channel when the torque member is in the normal position.

23. The releasable attachment system of claim 20 further including a torque ring mounted within the housing and fixed against rotation therein, the detent means being engageable between the torque ring and the torque member.

* * * * *